United States Patent [19]

Mehra

[11] Patent Number: 4,623,371

[45] Date of Patent: Nov. 18, 1986

[54] UTILIZING THE MEHRA PROCESS FOR PROCESSING AND BTU UPGRADING OF NITROGEN-RICH NATURAL GAS STREAMS

[75] Inventor: Yuv R. Mehra, Odessa, Tex.

[73] Assignee: El Paso Hydrocarbons Company, Odessa, Tex.

[21] Appl. No.: 759,327

[22] Filed: Jul. 26, 1985

Related U.S. Application Data

[63] Continuation-in-part of Ser. No. 637,210, Aug. 3, 1984, Pat. No. 4,578,094, which is a continuation-in-part of Ser. No. 532,005, Sep. 14, 1983, Pat. No. 4,526,594, which is a continuation-in-part of Ser. No. 507,564, Jun. 23, 1983, Pat. No. 4,511,381, which is a continuation-in-part of Ser. No. 374,270, May 3, 1982, Pat. No. 4,421,535.

[51] Int. Cl.$^4$ ................................. F25J 3/00
[52] U.S. Cl. ........................... 62/17; 62/20; 55/68; 55/76
[58] Field of Search ............... 62/17, 20; 55/68, 76

[56] References Cited

U.S. PATENT DOCUMENTS

| | | | |
|---|---|---|---|
| 1,768,521 | 6/1930 | Ayres, Jr. | 55/48 |
| 1,934,029 | 11/1933 | Asbury | 55/48 |
| 2,237,386 | 4/1941 | Carney | 55/48 |
| 2,521,233 | 9/1950 | Latchum, Jr. | 55/48 |
| 2,596,785 | 5/1952 | Nelly, Jr. et al. | 48/190 |
| 2,663,169 | 12/1953 | Twomey | 62/28 |
| 2,814,359 | 11/1957 | Koble | 55/48 |
| 3,097,924 | 7/1963 | Kinney et al. | 23/209 |
| 3,197,970 | 8/1965 | Nelson et al. | 62/17 |
| 3,202,482 | 8/1965 | Herster | 23/209 |
| 3,213,151 | 10/1965 | Sherk | 260/667 |
| 3,255,572 | 6/1966 | Miller et al. | 55/31 |
| 3,292,380 | 12/1966 | Bucklin | 62/20 |
| 3,455,116 | 7/1968 | Swift et al. | 62/17 |
| 4,158,556 | 6/1979 | Yearout | 62/28 |
| 4,272,269 | 6/1981 | Hammond et al. | 62/17 |
| 4,276,057 | 6/1981 | Becker et al. | 55/40 |
| 4,414,004 | 11/1983 | Wagner et al. | 55/48 |
| 4,466,946 | 8/1984 | Goddin, Jr. et al. | 423/228 |

OTHER PUBLICATIONS

"High $CO_2$-High $H_2S$ Removal with Selexol Solvent," by John W. Sweny, 59th Annual GPA Convention, Mar. 17-19, 1980, Houston, Texas.

"Gas Conditioning", under Natural Gas in vol. 11 of Kirk-Othmer Encyclopedia of Chemical Technology, 3rd Edition, 3/1980, pp. 638-641.

*Primary Examiner*—Ronald C. Capossela
*Attorney, Agent, or Firm*—Depaoli & O'Brien

[57] ABSTRACT

An improved Mehra process utilizes at least one and, if necessary, up to three gas extracting steps for processing a nitrogen-rich gas stream which can vary in composition from 3 to 75 mol. % nitrogen, the remainder being hydrocarbons, and from entirely dry to water saturated and from sweet to sour. The improved Mehra process provides up to three products, namely: nitrogen gas product, $C_1$-rich gas product and $C_2$+ liquid product. The process effectively utilizes a physical solvent for extracting and upgrading the BTU value of a nitrogen-rich natural gas stream.

36 Claims, 1 Drawing Figure

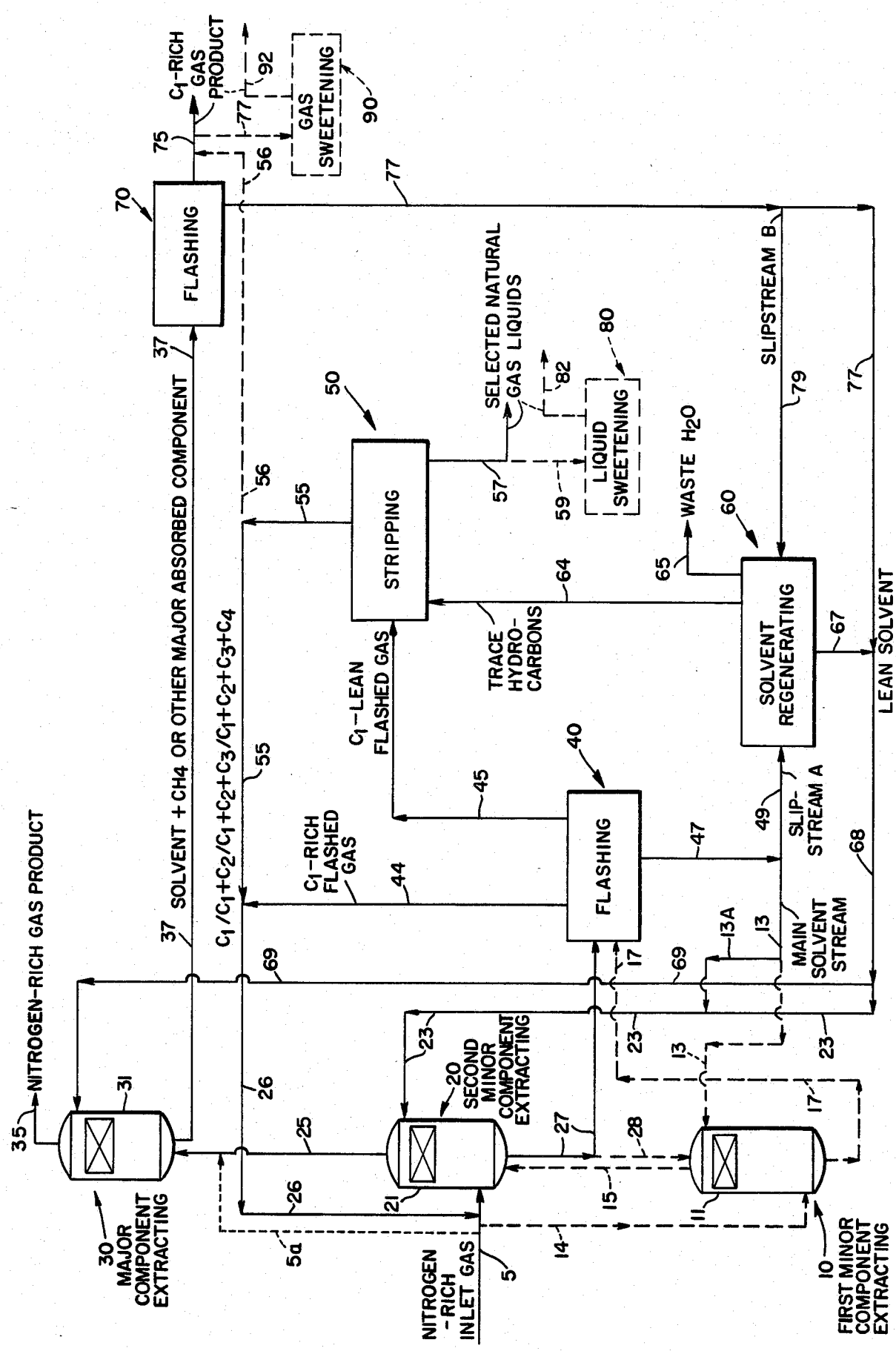

UTILIZING THE MEHRA PROCESS FOR PROCESSING AND BTU UPGRADING OF NITROGEN-RICH NATURAL GAS STREAMS

REFERENCE TO RELATED APPLICATIONS

This application is a continuation-in-part of co-pending application Ser. No. 637,210, filed Aug. 3, 1984 now U.S. Pat. No. 4,578,094, of Yuv R. Mehra, entitled "HYDROCARBON SEPARATION WITH A PHYSICAL SOLVENT", which is a continuation-in-part of application Ser. No. 532,005, filed Sept. 14, 1983, now U.S. Pat. No. 4,526,594, which is a continuation-in-part of application Ser. No. 507,564, filed June 23, 1983, now U.S. No. 4,511,381, which is a continuation-in-part of Ser. No. 374,270, filed May 3, 1982, now U.S. Pat. No. 4,421,535.

BACKGROUND OF THE INVENTION

1. Field of the Invention

This invention relates to the treatment of gaseous streams containing appreciable quantities of nitrogen. It more closely relates to removing and recovering methane and higher boiling hydrocarbons from a gas stream, natural or synthetic, which contains large quantities of nitrogen, may contain acidic components such as $CO_2$ and $H_2S$, and may vary in moisture content from dry to saturated. It specifically relates to the removal of nitrogen, which does not contribute to the heating value of natural gas streams in order to upgrade its heating value.

2. Review of the Prior Art

During recent years, there has been strong emphasis on the secondary and tertiary methods of recovering oil from formations where the primary oil-producing methods are no longer productive. Nitrogen injection for reviving these oil wells is not useful in most formations, but in some formations such as in the central Texas area, nitrogen injection has been successfully utilized for the recovery of additional oil.

After several years of nitrogen injections at high pressure, approximately 2000 psig, the nitrogen seems to have broken through the formations in many instances. In other words, nitrogen is coming out with the oil and it is separated from the oil at the separator. Previously, the associated gases were rich in hydrocarbons heavier than methane, along with substantial quantities of methane. The present dilution effect of nitrogen has caused the same associated wellhead gas to have an extremely low BTU content, thereby making it unsuitable for pipeline shipments. If the natural gas contains more than 3% of nitrogen, it is off specification for most of the world's pipelines.

This situation has caused the oil producer to curtail oil production because he cannot burn the nitrogen-rich gas, and environmental laws prohibit him from venting the associated hydrocarbons. The oil producer is thus limited to the choice of technology available to him for properly processing the associated gases from an oil well. The available technology involves cryogenic principles, thereby causing the purified gas to be uneconomical in the natural gas market, even after subsidization with the revenues from oil production.

Natural gas is a mixture of hydrocarbons, including methane, ethane, propane, and various various amounts of higher molecular weight hydrocarbons together with nitrogen and acid gases, such as $CO_2$ and/or $H_2S$. A "dry" gas is one containing predominantly methane with some ethane, propane, and butane and having a very low hydrocarbon dew point. The heavier the hydrocarbons, such as pentane and higher homologs, that are present in the gas, the higher the hydrocarbon dew point. For pipeline transmission, enough of the heavier hydrocarbons must be removed to lower the dew point without losing too many BTUs to meet specifications. In the past, gas with large quantities of high molecular weight hydrocarbons have been passed through gasoline extraction plants and/or dew point control stations to lower the dew point. Also, frequently the gas has required conditioning to remove sulfur compounds and carbon dioxide.

A natural gas stream coming from the wellhead is also usually saturated with water at its ambient temperature which may have a range of 75°–120° F. so that its water content may vary from 20 pounds to more than 50 pounds per million standard cubic feet. However, difficulties are frequently met while pumping such natural gas, such as formation of ice and hydrates or the accumulation of water which can block the flow as well as cause corrosion, unless the water content is reduced to a value of less than 12 pounds, preferably less than 7 pounds, of water per million standard cubic feet of natural gas. In terms of dew point, a natural gas having a dew point of 30° F., preferably 20° F. or lower, is generally considered safe for transportation in a pipeline. Dehydration can be carried out under a wide range of pressures from 15 to 5,000 psig, but it is usually carried out at pipeline pressures of 500–1,500 psig.

Dehydration and sweetening of natural gas has been done with physical solvents, as taught in U.S. Pat. Nos. 3,362,133, 3,770,622, and 3,837,143, but always with an economic penalty from loss of hydrocarbons that were absorbed with the acid gases. Such losses are understandable when comparing the relative solubilities of the acid gases and of the hydrocarbons in physical solvents.

Such solubilities of hydrocarbon gases are disclosed in a paper entitled "High $C_2$-High $H_2S$ Removal With SELEXOL Solvent", that was presented by John W. Sweny at the 50th Annual Gas Processors Association Convention, Mar. 17–19, 1980, the relative solubility of $CO_2$ over methane in a mixture of dimethyl ethers of polyethylene glycol (DMPEG) is 15.0 and the relative solubilities of various hydrocarbons present in a natural gas stream are disclosed as varying from 6.4 to about 165, whereas the similar relative solubility of water is 11,000.

The Mehra process capitalized on the liabilities of the prior art processes by utilizing the relative solubilities of the hydrocarbons in physical solvents. Specifically, the Mehra process handles any natural gas, from very sour to entirely sweet, in the same equipment while simultaneously dehydrating the gas and recovering the heavier hydrocarbons with a physical solvent, as disclosed in U.S. Pat. Nos. 4,421,535 and 4,511,381 of Yuv R. Mehra, both of which are herein incorporated by reference. The compositions of its liquid hydrocarbon product and of its residue natural gas product can be readily adjusted in accordance with market conditions so that profitability of the extraction operation can be maximized at all times and on short notice. This process thereby produces a liquid hydrocarbon product having a composition which is selectively versatile rather than fixed, as in prior art processes.

The absorption principle leads to an alpha or relative volatility for methane with respect to ethane of slightly less than 5 for almost all known absorption liquids. However, the relative volatility for methane with respect to ethane in the presence of dimethyl ether of polyethylene glycol (DMPEG) is 6.4, indicating that it is more selective toward ethane than other absorption liquids. N-methyl pyrrolidone (NMP) and dimethyl formamide (DMF) have relative volatilities for methane/ethane of 5.3 and 8.5, respectively. However, the solubility of hydrocarbons in NMP is 0.03 standard cubic feet per gallon (SCF/gal) and in DMF is 0.04 SCF/gal; these are low when compared to 1.0 SCF/gal for DMPEG. The relative volatility of nitrogen over methane is 5.0.

Therefore, it is the combination of improved selectivity towards ethane and the hydrocarbon loading capacity of dimethyl ether of polyethylene glycol that makes it a superior absorption solvent for separating and recovering the components of a natural gas stream that are heavier than methane. The minimum qualifications for a physical solvent are a minimum relative volatility of methane over ethane of 5.0 (thereby defining its improved selectivity toward ethane over methane) and minimum solubility of 0.25 standard cubic feet per gallon of the solvent (thereby defining its hydrocarbon loading capacity). However, the ideal physical solvent would have a selectivity toward ethane over methane as high as 10.0, and simultaneously would possess a hydrocarbon loading capacity of about 3.0 SCF/gal. This combination also enables solvent flow rate variation and flashing-pressure variations to be particularly useful for flexibly producing liquid products, having selected hydrocarbon compositions.

This physical solvent is selected from the group consisting of dialkyl ethers of polyalkylene glycol, N-methyl pyrrolidone, dimethyl formamide, propylene carbonate, sulfolane, and glycol triacetate. The solvent is preferably selected from the group consisting of dimethyl ether of polyethylene glycol, dimethyl ether of polypropylene glycol, dimethyl ether of tetramethylene glycol, and mixtures thereof, and the solvent most preferably is dimethyl ether of polyethylene glycol containing 3-10 ethylene units and having a molecular weight of 146 to 476.

The glycol can be branched, such as polypropylene glycol. The basic difference between the behaviors of ethyl and propyl groups is the affinity for water for the ethyl and greater affinity for hydrocarbons for the propyl group. A mixture of dimethyl ethers of polyethylene and polypropylene glycol in various combinations is consequently suitable for recovering ethane plus heavier hydrocarbons from a natural gas. In such a mixture, the content of dialkyl ether of polyethylene glycol should be a minimum of 20% by volume, with dialkyl ether of polypropylene glycol being limited to 80% by volume maximum.

The versatility of the Mehra process is achieved by flexibility in certain operating conditions and by use of certain additional steps that are not used in the prior art. These conditions and steps are listed as follows, in order of importance:

(1) varying the flow rate of a physical solvent with respect to flow rate of the natural gas stream in an extraction column to produce the rich solvent;

(2) varying the flashing pressure for one or more of the successive flashing stages for the rich solvent;

(3) recycling the flashed $C_1$ + undesirable gases from the first flashing stage and, selectively, also the second flashing stage to the extraction column;

(4) compressing, cooling, and condensing the flashed gases from the remaining flashing stages to form a crude liquid;

(5) rejecting and returning to the residue gas line selected components of the crude liquid, viz., methane (demethanizing), methane plus ethane (de-ethanizing), methane, ethane, and propane (depropanizing), or methane, ethane, propane, and butanes (debutanizing) in a stripping column for the crude liquid by:
  (a) varying the pressure in the column, and
  (b) varying the temperature at the bottom of the column; and (6) recovering the remaining components as the natural gas liquid product.

However, daily changes in market conditions may also cause the price of a single liquid hydrocarbon heavier than ethane to drop below its fuel price so that this hydrocarbon should be selectively rejected, but there was no way in the prior art or in these two patents of doing so without also rejecting all components of lower molecular weight. For example, if the price of ethane was below its fuel value, it could be rejected with methane, as taught in U.S. Pat. Nos. 4,421,535 and 4,511,585, but if the price of propane was below its fuel value while the price of ethane was above its fuel value, both of these hydrocarbons would have to be rejected together because no method existed for separating them. Accordingly, U.S. Pat. No. 4,526,594 of Yuv R. Mehra, which is also incorporated herein by reference, provides a process that is useful when changes in the market prices for individual hydrocarbons in liquid form cause the market price for an individual hydrocarbon liquid to fall below its fuel price. Such prices change on a daily basis so that it becomes advantageous to be able to extract all of the $C_2-C_5+$ hydrocarbon liquids while rejecting and returning to the residue gas line one or more of the $C_2-C_4$ hydrocarbons that are priced below their fuel values. The extraction plant can thereby be operated at optimum profit levels at all times.

The process of U.S. Pat. No. 4,526,594 accomplishes this selective rejection by subjecting the rejected components of the crude liquid to a second extraction with a portion of the same physical solvent to produce a gas stream of $C_1$ or $C_1+C_2$, which is returned to the residue gas line, and a second rich solvent stream which is singly flashed to produce an overhead gas stream and a liquid mixture which is regenerated to produce the physical solvent stream for the extracting. This gas stream is compressed, cooled, and condensed to form a second crude liquid stream. This liquid stream is split. The bottom portion, of $C_3$ or $C_3+C_4$'s or $C_4$'s only, is sent to the residue gas line, and the top portion, of $C_2$ or $C_2+C_3$ or $C_3$ only, is combined with the liquid product from the stripping column.

$CO_2$ and $H_2S$ have solubilities in DMPEG that are very close to the solubilities of propane and pentane in this solvent. Therefore, it is difficult to separate these acidic materials from the desirable gases when treating sour natural gas. The prior art has tended to perform this separation before removing hydrocarbons, thereby requiring large-capacity equipment and losing significant quantities of desirable hydrocarbons with $CO_2$ and $H_2S$ vent streams. Widespread usage of DMPEG has obviously been avoided.

In one of the embodiments of the Mehra process, $CO_2$ and $H_2S$ are allowed to remain with the desirable gases until final stages in the process where they are removed as liquids, thereby requiring smaller and less expensive equipment because the equipment's size is determined by mode of treating, i.e., in gas phase or liquid phase.

This treatment procedure requires the usage of substantially larger quantities of DMPEG than has been recommended by the prior art, since the quantity of $C_2+$ hydrocarbons is generally larger than the quantities of $CO_2$ and $H_2S$ in a relatively sweet natural gas stream. There is, consequently, enough absorption capacity in the DMPEG stream when equilibrium is reached that the acidic materials in the recycle stream and in the sour natural gas can be completely removed, thereby producing a sweet methane-rich stream from the top of the extractor that meets pipeline specifications.

The advantage of this treatment method over those of the prior art is that a single plant can accept a very wide variety of natural gas streams, from very acidic to completely sweet, simply by utilizing the acid removal unit (e.g., an amines process) to a selective extent or even by by-passing it entirely. Although liquid-phase sweetening requires a lower capital investment and has lower operating costs than gas-phase sweetening, there are compensating factors in favor of gas-phase sweetening. These include the use and pumping of smaller quantities of solvent and the availability of maximum flexibility as to hydrocarbon composition in the liquid product.

It is preferred that amine processes (MEA, DEA, or DGA) be utilized for removing acid gas components ($CO_2$ and $H_2S$) in gas phase before proceeding with this invention process. The sweet natural gas thus produced will be saturated with water vapor at the pipeline pressures and operating temperatures because any amine process is aqueous based and introduces water vapor into the natural gas stream.

Alternatively, acid gas components can be removed in the liquid phase downstream of processing according to this invention process by amine processes using MEA or DEA. For maximum flexibility of recovering ethane versus rejecting ethane while recovering all of propane plus heavier hydrocarbons in contrast to recovering propane versus rejecting ethane and propane while recovering all of butane plus heavier hydrocarbons, it is preferred that the sour natural gas stream be treated with aqueous amine processes in gas-phase operation in order to extract $CO_2$ and $H_2S$ components without losing any hydrocarbons.

Because natural gas is normally in a water-saturated state, much water must be extracted and carried by the solvent through one or more flashing stages of the Mehra process and then removed from the solvent by regenerating its entire volume at a temperature of about 300° F., with subsequent cooling to ambient temperature. Such heating and cooling is quite expensive, and Ser. No. 637,210 provides a process for minimizing energy consumption for separating hydrocarbons and water from the solvent. The process is useful for an inlet natural gas stream containing at least 0.2 mol or vol. percent of $C_5+$ hydrocarbons and comprises dividing the solvent stream and then selectively extracting the gas stream in a first extraction stage with the major solvent stream and in a second extraction stage with the minor solvent stream. The major stream contains up to an equilibrium amount of $C_5+$ hydrocarbons, and the minor stream is lean with respect to $C_1+$ hydrocarbons and dry with respect to water. The minor solvent stream or slipstream is generally all of the solvent that is regenerated. It is always less than 25% of the total amount of solvent and always sufficient to remove the water and $C_5+$ hydrocarbons from the natural gas stream.

U.S. Pat. No. 1,768,521 teaches the two-stage absorption of natural gas, using a completely stripped absorption oil for feeding to a second absorber and the semi-rich oil from this absorber for feeding to the first absorber.

U.S. Pat. No. 1,934,029 describes a process for: (a) separating hydrogen from gaseous hydrocarbons by extracting a mixture thereof with a hydrocarbon oil, (b) separating hydrogen and nitrogen with ethyl ethers, acetic acid, and amyl alcohol, (c) separating hydrogen and sulfur dioxide with benzene and nitrobenzene, and (d) separating hydrogen and ammonia or hydrogen and carbon monoxide with alcohols.

U.S. Pat. No. 2,237,386 discloses a process in which three absorbers are utilized for successively removing hydrocarbons from an inlet gas stream by initially removing $C_5+$ hydrocarbons and butane partially therefrom, next for completely removing butane and partially removing propane, and finally for completely removing propane and partially removing methane and ethane.

U.S. Pat. No. 2,521,233 teaches the removal of nitrogen from natural gas by using liquid ammonia as a solvent so that gas from a carbon dioxide well containing large amounts of nitrogen and carbon dioxide can be purified by drying the gas and cleaning it at about 700 psi and 70°–110° F.

U.S. Pat. No. 2,596,785 describes a method for enriching natural gas by initial removal of $CO_2$ and $H_2S$, dehydration, and refrigeration to a temperature of $-110°$ F. before absorption with a lean oil to produce an enriched gas and a residue gas containing 60% nitrogen and having a heating value of approximately 450 BTU per cubic foot.

U.S. Pat. No. 2,663,169 relates to nitrogen-contaminated natural gases containing up to 40% by volume of nitrogen. The feed gas, after removal of water vapor and carbon dioxide, is at 305° F. and is then sufficiently cooled such that nitrogen and $C_3+$ hydrocarbons can be condensed and removed.

U.S. Pat. No. 2,814,359 relates to treatment of an off-gas from furnace manufacture of carbon black by absorption with dimethyl formamide. Nitrogen is absorbed, but hydrogen is not, so that these two gases are separated. In addition, carbon dioxide, acetylene, heavier acetylenes, and small quantities of other substances such as argon, benzene, vinyl acetylene, hydrogen sulfide, carbonyl sulfide, and carbon disulfide are similarly removed by absorption.

U.S. Pat. No. 3,255,572 is directed to scrubbing a natural gas containing hydrocarbons, carbon dioxides, and water with nitromethane absorbent and then with glycol absorbent in a two-stage absorption process. Nitromethane may also be used as a mixture with an inert solvent which is up to 50% by volume of the mixture. Suitable inert solvents include propylene carbonate, ethylene carbonate, N,N'-dimethylformamide, hydrocrylonitrile, formamide and gamma-butyrolactone.

U.S. Pat. No. 4,414,004 describes a process for removing condensable aliphatic hydrocarbons and acidic gases from natural gas containing these materials, wherein the natural gas is initially treated at superatmospheric pressure with polyethylene glycol dialkyl ethers, as the solvent, in a first absorption stage to effect absorption of the condensable aliphatic hydrocarbons. The natural gas from this first stage is then treated with the same solvent under superatmospheric pressure in a second absorption stage to completely or partly absorb the acidic gases. The solvent charged with the condensable aliphatic hydrocarbons from the first stage is treated with water in an extraction stage to form a hydrocarbon phase containing the condensable aliphatic hydrocarbons and an aqueous dialkyl ether phase, and the hydrocarbon phase is then separated from the aqueous dialkyl ether phase. The solvent charged with acid gases from the second stage is regenerated by expansion and/or stripping, and the regenerated solvent is recycled to the absorption stages.

U.S. Pat. No. 4,466,946 relates to a process for treating low quality natural gases containing 30–40 mol % of $CO_2$, as is now produced by $CO_2$ miscible flooding of low quality and sour gas reservoirs for enhanced oil recovery. According to one embodiment, at least a portion of the heavy hydrocarbons are removed by chilling, prior to a $CO_2$ absorption stage that employs an aqueous alkanolamine solution. For example, triethanolamine absorption may be followed by diethanolamine absorption and then by sweetening by absorption with a mixture of polyethylene glycol dialkyl ethers.

There is consequently a need for a simple and inexpensive process that is operable at the wellhead to separate nitrogen from the natural gas. There is further a need for a process that can dehydrate, sweeten, and selectively separate $C_2+$ hydrocarbons from methane in the natural gas during or prior to separating nitrogen therefrom.

SUMMARY OF THE INVENTION

The object of this invention is to provide a process for separating nitrogen from a hydrocarbon gas mixture by treatment with a physical solvent in order to upgrade its specific BTU values.

Another object is to provide a means for processing a natural gas stream that is rich in nitrogen by utilizing a physical solvent for extracting ethane and heavier hydrocarbons from both methane and nitrogen and then again utilizing the physical solvent for extracting the methane from the nitrogen, thereby forming three separate streams which leave this improved Mehra process.

A further object is to dehydrate, sweeten, and selectively separate $C_2+$ hydrocarbons from a sour natural gas stream that is rich in $N_2$, then to separate nitrogen from the remaining methane, and finally to remove the sour gases from the $C_2+$ hydrocarbons.

These objectives are achieved, according to the principles of this invention, by a process utilizing at least one and, if necessary, two or three gas contacting steps for treating a nitrogen-rich gas stream which can vary in composition from 3 to 75 mol % nitrogen, the remainder being hydrocarbons in a sweet natural gas. The first one and possibly two gas contacting steps are employed for selective removal by extraction of all component materials except the nitrogen and methane; because these extracted materials are minor components of the natural gas stream, these steps are hereinafter referred to as minor-component extraction. The remaining gas contacting step is for extraction of the methane; because methane is typically the major component of natural gas, this step is hereinafter referred to as major-component extraction. The pressures of the minor-component and major-component extractions can vary between 300 and 1,300 psig.

The natural gas stream is first countercurrently contacted, for minor-component extraction, with a physical solvent in liquid form, whereby water, if present, and $C_2+$ hydrocarbons, accompanied by some methane, are extracted to form a rich solvent which is flashed in at least one stage and to at least an intermediate pressure to produce a $C_1$-rich flashed gas and a $C_1$-lean flashed gas. The former is recycled to the contacting step; the latter is sent, after compressing, cooling, and condensing, as a liquid stream to a stripping operation which selectively demethanizes, de-ethanizes, depropanizes, or debutanizes the natural gas liquids to produce a liquid hydrocarbon product which is selectively adjustable, substantially to any selected degree, in response to market demands. It should be understood that the name given to the stripping operation (e.g., depropanizing) indicates that the lower-molecular weight hydrocarbons are removed along with the named hydrocarbon. For example, "depropanizing" signifies the removal of $C_1+C_2+C_3$.

In order to separate the nitrogen from the methane by major-component extraction, the residue natural gas from the minor-component extraction is again extracted with a sufficient proportion of lean-and-dry solvent that substantially all of the $C_1+$ hydrocarbons are removed from the nitrogen which is then injected into the ground, vented to the atmosphere, or utilized for any other purpose. The methane-rich solvent is flashed to a significantly lower pressure, sufficient to release the methane from the solvent. The solvent may then be sent to the regeneration operation, in whole or in part, or may be re-used, because of its dryness and leanness, for the extraction of the residue natural gas from the minor-component extraction.

In the process of this invention as exemplified by nitrogen-rich natural gas, three products are made: namely, a nitrogen product, a methane-rich gas product, and a $C_2+$ liquid product. The nitrogen content of either methane-rich gas stream is generally less than 3 mol %. The nitrogen stream, containing minor quantities of methane, can be further compressed for delivery to nitrogen injection facilities or, depending upon the economics and quantity of nitrogen availability, can be vented safely to atmosphere without violating any environmental laws. Should it be necessary to vent such a nitrogen stream and if economically viable, it is preferred to recover energy from the nitrogen stream by reducing its pressure through a power recovery turbine, such as a gas expander driving a compressor unit.

The solvent separated in the flashing stage from the major-component extracting may be partially regenerated in a solvent regenerator where any water, if present in the inlet gas stream, is discarded. The same solvent regenerator can serve both the minor-component extraction and the major-component extraction.

The minor-component extraction operation may be single stage or dual stage, but the residual natural gas meets pipeline specifications with respect to water content and acid gas content after even a single stage. Two-stage minor-component extraction, using a selectively lean-and-dry solvent for the second stage, is less expensive, however. The determining factor is generally the $C_5+$ content of the inlet natural gas stream; if greater than 2 mol %, two sequentially operated minor-component extraction stages are preferred.

If the minor-component extraction is two stage, 75-90% of the minor-component extraction solvent is typically not regenerated but is used directly, after the final flashing stage, for extracting heavier hydrocarbons from the inlet natural gas stream as it enters the process. This partially stripped natural gas stream leaving the first minor-component extraction stage may be substantially dehydrated but may not be substantially stripped of hydrocarbons, depending upon the composition of the inlet natural gas.

The partially stripped natural gas stream is then countercurrently contacted in the second minor-component extraction stage by a lean-and-dry solvent stream which has been regenerated to a moisture content equivalent to less than 7 pounds of water per million standard cubic feet in the residue natural gas stream and less than 1 vol. % of $C_5+$ hydrocarbons. The residue gas leaving this second minor-component stage meets pipeline specifications except for its nitrogen content.

If the nitrogen-rich inlet or feed gas stream is lean in hydrocarbons heavier than butane, this stream can flow directly to the second minor-component extraction stage, thus bypassing the first minor-component extraction stage which would be obviously uneconomical. If the nitrogen-rich inlet or feed gas stream is lean in hydrocarbons heavier than methane, this stream can flow directly to the major-component extraction stage, because both of the minor-component extraction stages would be obviously uneconomical.

BRIEF DESCRIPTION OF THE DRAWING

The FIGURE is a schematic flow sheet of the process in which some of the unit operations are shown as block diagrams.

DESCRIPTION OF THE PREFERRED EMBODIMENTS

The process shown schematically in the FIGURE comprises extraction units 10, 20, 30, a flashing unit 40 having at least one flashing stage, a stripping unit 50, a solvent regenerating unit 60, and a major-component flashing unit 70, consisting of at least one flashing stage. Extraction units 10 and 20 are the minor-component extraction stages, which may be combined in a single vessel but which are shown in the drawing as two vessels for illustrating their functions. These are a first vessel 11 and a second vessel 21. The pipelines conveying gas and liquid streams in the FIGURE are illustrated without flow control valves which are to be understood as conventionally used in appropriate places, particularly for diversion of flow from one pipeline to another. Similarly, coolers and compressors are likewise to be understood as being used where appropriate.

Referring to the FIGURE, a natural gas stream in line 5, normally saturated with water but in some circumstances completely dry, enters extraction stage 10 or 20, depending upon its content of $C_5+$ hydrocarbons. This natural gas stream is joined by a stream of flashed gases in line 26, mostly $C_1$ through $C_4$. If the $C_5+$ content of the natural gas stream in line 5 is greater than 2 mol %, extraction unit 10 may be included in the process by sending the $N_2$-rich inlet gas stream through line 14 to vessel 11; if the $C_5+$ content is less than 2 mol %, stage 10 may be included in the process by sending the $N_2$-rich gas stream through line 14 to vessel 11.

EXAMPLE I

Inlet Gas Stream Containing More than 2 Mol % $C_5+$

Assuming that the gas stream in line 5 contains more than 2 mol % $C_5+$, it enters the bottom of first extraction stage vessel 11 through line 14. A main solvent stream in line 13, containing less than 15 mol % $C_5+$ hydrocarbons, enters the top of vessel 11 and may be augmented by enriched solvent entering the top of vessel 11 through line 28. The solvent flows downwardly and counter-currently to the upwardly flowing natural gas. A stream of rich solvent in line 17 leaves the bottom of vessel 11 to enter flashing unit 40.

The partially stripped natural gas leaves the top of vessel 11 through line 15 and enters the bottom of the second extraction stage in vessel 21. A stream of lean-and-dry solvent, containing less than 1 wt. % of water and less than 1 volume % of $C_5+$ hydrocarbons, enters the top of vessel 21 through line 23 and flows downwardly, countercurrently to the upwardly flowing natural gas, until it either departs as enriched solvent through line 27 or selectively enters the top of vessel 11 through line 28. Alternatively, the enriched solvent may entirely bypass vessel 11 to enter flashing unit 40 through line 27. The residue natural gas, in equilibrium with the lean-and-dry solvent in line 23, leaves vessel 21 through line 25; it is very dry with respect to water and very lean with respect to $C_2+$ hydrocarbons, depending upon the economically desired NGL product composition, but it contains nearly all of its methane and nitrogen.

The enriched solvent in line 17 plus the rich solvent in line 27 are flashed in flashing unit 40 in at least one stage and to at least an intermediate pressure. If two flashing stages are employed, the first stage releases $C_1$-rich flashed gases which leave unit 40 through line 44 and return to inlet gas line 5 via line 26 and a compressor. The second flashing stage releases $C_1$-lean flashed gases which pass through line 45, another compressor, and a condenser for further treatment in stripping unit 50.

Stripping unit 50 may be operated as a demethanizer, a de-ethanizer, a depropanizer, or a debutanizer, respectively removing all or selected portions of $C_1$, $C_1+C_2$, $C_1+C_2+C_3$, or $C_1+C_2+C_3+C_4$ hydrocarbons as overhead. Stripping unit 50 comprises at least a stripping column, a recirculating line, and a reboiler. The selected $C_1$-$C_4$ gases are removed from the incoming liquid in the stripping column and pass through line 55 and a compressor to join line 26 and ultimately line 5, whereby the $C_1$-$C_4$ gases become a part of the inlet gas stream. Selected $C_2$-$C_5+$ natural gas liquids leave as product through line 57.

A stream of solvent, which has been stripped of $C_1+$ hydrocarbons and contains water and no more than 15 mol % $C_5+$ hydrocarbons, leaves flashing unit 40 through line 47. After removal of a slipstream A thereof through line 49, the remainder of the main solvent stream flows through line 13 to enter the top of vessel 11 or through line 13A to join line 23 and enter the top of vessel 21.

Slipstream A in line 49 enters solvent regenerating unit 60, wherein circulation through a reboiler distills water and hydrocarbons from the solvent to form a condensed overhead stream containing both waste water and $C_5+$ hydrocarbons. These are separated by decanting. A stream of waste water leaves through line 65, and a trace stream of hydrocarbons also leaves solvent regenerating unit 60 through line 64 to enter stripping unit 50. The lean-and-dry solvent produced by solvent regenerating unit 60 passes through lines 67 and 68 and a cooler to enter the second minor-component extracting stage in vessel 21 through line 23 and the major-component extracting stage in vessel 31 through line 69.

The process shown in the FIGURE and described hereinbefore is primarily designed for removing all of $C_2+$ hydrocarbons in the second minor-component extracting stage and for removing major portions of water and $C_5+$ hydrocarbons in the first minor-component extracting stage. The respective volumes of the minor and major solvent streams for these two stages are determined by the respective quantities of water, $C_2$-$C_4$ hydrocarbons, and $C_5+$ hydrocarbons, the loading capacities of the solvent for the hydrocarbons to be extracted, and relative solubilities in the solvent of the $C_2+$ hydrocarbons with respect to methane.

The residue gas stream in line 25 still contains essentially all of its nitrogen as it enters extractor vessel 31 of major-component extracting unit 30, while a lean-and-dry solvent stream in line 69 enters the top of vessel 31 to flow downwardly and countercurrently to the upward flow of the gas. The quantity of the solvent flow in line 69 is sufficient to extract substantially all of the methane and little of the nitrogen.

Residual nitrogen leaves the top of unit 30 through line 35. It is at a pressure not far below its inlet pressure and can readily be compressed by a compressor and injected into the ground through suitable injection wells. Alternatively, if economically justifiable, the nitrogen stream can be passed through a gas expansion turbine for power recovery before venting to the atmosphere.

The methane-rich solvent leaves extraction unit 30 through line 37 to enter flashing stage 70 wherein the pressure is reduced substantially to a level where all dissolved components are released in at least one flashing stage. Methane is released through line 75 as methane-rich gas product. Its pressure may be increased by a compressor, and the pressurized methane is discharged to a pipeline while meeting its pipeline specifications. However, in the event that it is economically beneficial to enrich the methane stream in line 75 with higher-molecular weight hydrocarbons, all or a portion of the flashed-off gases in line 55 can be diverted through line 56 to join line 75.

The stripped solvent leaves flashing stage 70 through line 77. If it is sufficiently lean that it will avidly absorb the methane and contains less than 1 vol. % of $C_5+$ hydrocarbons, all or a portion of the solvent stream in line 77 can be recycled to join the freshly regenerated solvent in line 67, if any is needed, for forming the lean-and-dry solvent feed stream in line 68 which is used for extraction units 20 and 30. The remaining solvent, if any, moves through line 79 as a slipstream B to join the solvent slipstream A in line 49 that is to be regenerated in solvent regenerating unit 60.

EXAMPLE 2

Inlet Gas Stream Containing Less Than 2 Mol % $C_5+$

It naturally follows that if the inlet natural gas stream is reasonably lean with respect to $C_5+$ hydrocarbons, the first extraction stage can be omitted from the process. The natural gas then flows from line 5 into vessel 21, wherein the major solvent stream that enters vessel 21 through line 23 via line 13A removes whatever $C_2+$ hydrocarbons that are present in the upwardly flowing gas in addition to the water and acidic impurities that are in the gas. Lines 13, 14, 15, 17, and 28, servicing vessel 11, become inoperative. The stripped gas that then enters vessel 31 through line 25 contains essentially nothing but nitrogen and methane plus minor quantities of undesirable components. Flashing in flashing units 40, 70, stripping in unit 50, and regenerating in unit 60 are then carried out in a similar manner, as described in Example 1.

However, if the content of heavier hydrocarbons in $N_2$-rich natural gas streams within line 5 is such that it is economically preferable not to extract these heavier hydrocarbons, the inlet natural gas stream can directly enter the major-component extracting vessel 31 via line 5a. Thus, all the heavier hydrocarbons would be extracted along with the methane from the $N_2$-rich stream and would leave vessel 31 with the physical solvent in line 37 and form a combined hydrocarbon/gas product stream, rich in methane, that would leave the process via line 75 after having been stripped from the solvent by flashing.

Flashing the enriched solvent stream, the rich solvent stream, or a mixture of these solvent streams to approximately atmospheric pressure in at least two stages provides optimum efficiency for this improved Mehra process. Nevertheless, there are some small plants which have insufficient throughput, such as approximately one million cubic feet of raw natural gas per day, to justify a compressor for the $C_1$-rich flashed gases. For such small plants, it is economically preferable to use a single flashing stage which produces a single flashed gas stream of $C_2+$ hydrocarbons (plus possibly substantial amounts of methane) for feeding to the demethanizer. This modification of the Mehra process imposes a heavier load on the demethanizer and higher operating costs for demethanizing, but it saves on capital expenditures.

The pressure drop in the single flashing stage should reduce the pressure from wellhead or line pressure of up to 1300 psia to a pressure as low as 2 psia, but the exemplary terminal pressure after flashing may be 100 psia, 50 psia, atmospheric pressure, or, rarely, a vacuum, depending upon plant conditions which may include piggy-back utilizatioh of existing plant equipment. In contrast, plants having a very large throughput may utilize as many as eight flashing stages, having a ratio of absolute pressure of successive flashing stages of at least 2.0, in order to minimize energy consumption.

Any pressure drop and any number of flashing stages can be utilized for the Mehra process in general and for this improvement thereof, but it is preferred that at least two flashing stages be used in order to increase flashing efficiency and especially to be able to isolate and recycle to the extractor the stream of $C_1$-rich flashed gases without having to additionally compress and condense these gases and then pass them through the demethanizer.

Whether the inlet nitrogen-rich natural gas stream is sweet or sour, the $C_1$-lean flashed gases must be treated to prevent hydrate formation if they are to be condensed and the natural gas liquids are to be retrieved as a product. A preferred method for preventing hydrate formation is to inject methanol into the $C_1$-lean flashed gases preferably before the condensing step and definitely before the hydrate formation temperature is reached. This method is disclosed in a U.S. application Ser. No. 758,351 filed on July 24, 1985, which is entitled "PROCESS FOR FREEZE PROTECTION AND PURIFICATION OF NATURAL GAS LIQUID PRODUCT STREAMS PRODUCED BY THE MEHRA PROCESS" and which is fully incorporated herein by reference.

If, however, the natural gas liquids are to be left in gaseous form with a major absorbed component, e.g., methane, as is often necessary for plants located in isolated areas or with quite small throughputs, such treatment to prevent hydrate formation is not necessary. Further, if the nitrogen-rich inlet natural gas stream is dry, from a water-content standpoint, and natural gas liquids are desired as a product, methanol injection will not be needed to prevent hydrate formation but will be needed to remove traces of solvent in order to meet specifications for gumming compounds in the natural gas liquids leaving the process through line 57.

If the nitrogen-rich gas stream in line 5 contains both $C_2+$ hydrocarbons and acidic compounds such as $CO_2$ and $H_2S$, the acidic compounds will be extracted with the hydrocarbons and released by flashing unit 40 with the selected natural gas liquids discharged as product through line 57. In order for these liquids to meet product specifications, they must be sent through line 59 to a liquid sweetening unit 80 which removes the acidic compounds and produces a sweetened natural gas liquid product discharged through line 82.

More specifically, if an acidic nitrogen-rich gas stream in line 5 is also rich in $C_5+$ hydrocarbons, it flows through line 14 to first minor-component extracting vessel 11. Acidic compounds, $C_2+$ hydrocarbons, and whatever water is present in the inlet gas stream are removed in vessels 11 and 21 and sent to flashing unit 40 through line 17 and 27 and then pass through aqueous amine treating unit 80 with the natural gas liquids in lines 57 and 59.

If an acidic nitrogen-rich gas stream is lean in $C_5+$ hydrocarbons, it preferably flows through line 5 directly into second minor-component extracting vessel 21, wherein $C_2+$ hydrocarbons and all acidic compounds are removed, with whatever water exists in the inlet gas stream, by solvent from line 23. The enriched solvent, containing all of these extracted materials, flows through line 27 to flashing unit 40, and the acidic compounds leave through lines 57 and 59 with the liquid-phase hydrocarbons and are then removed therefrom by aqueous amine treating unit 80.

If an acidic nitrogen-rich gas stream is lean in $C_2+$ hydrocarbons, it is preferably sweetened before entering line 5. Alternatively, however, it may flow through line 5a to join line 25 and enter major-component extracting vessel 31, wherein $C_1+$ hydrocarbons, the acidic compounds, and water are removed by a sufficient volume of adequately lean-and-dry solvent in line 69, thereby releasing the nitrogen through line 35. The acidic compounds remain with the solvent and $C_1+$ hydrocarbons in line 37 and continue to remain with the $C_1$-rich gas product in line 75. If this necessarily gaseous product is to be sold as a sweet gas, it must then pass through a gas phase aqueous amine treating unit 90 for discharge through line 92.

Because it will be readily apparent to those skilled in the art of treating natural gas that innumerable variations, modifications, amplifications, and extensions of the examples and principles hereinbefore set forth can be made without departing from the spirit and the scope of the invention, what is hereby defined as such scope and is desired to be protected should be measured, and the invention should be limited, only by the following claims.

What is claimed is:

1. A process for separating $C_1+$ hydrocarbons and nitrogen from a nitrogen-rich natural gas stream which contains more than 3 mol % of said nitrogen, comprising the following steps:
   A. extracting said natural gas stream with a physical solvent to produce a nitrogen stream and a methane-rich solvent stream;
   B. flashing said solvent stream at a flashing pressure which is selected to be in between 1300 psia and 2 psia and is sufficiently low that substantially all said $C_1+$ hydrocarbons are separated from a stripped solvent stream and are produced as a stream of flashed-off gases; and
   C. recycling said stripped solvent stream to said extracting of said Step A.

2. The process of claim 1, wherein said nitrogen stream is passed through a power recovery turbine.

3. The process of claim 1, wherein said flashing utilizes up to eight flashing stages, having a ratio of absolute pressures between successive said flashing stages of at least 2.0.

4. The process of claim 1, wherein said flashed-off gases are compressed and cooled to form a $C_1$-rich gas product.

5. The process of claim 4, wherein:
   A. said nitrogen-rich natural gas stream contains $C_2+$ hydrocarbons and is lean with respect to $C_5+$ hydrocarbons; and
   B. said nitrogen-rich natural gas stream is extracted in one stage with said physical solvent to remove said $C_2+$ hydrocarbons and produce a residue natural gas stream primarily comprising nitrogen and methane for further extracting in said Step A of claim 1.

6. The process of claim 4, wherein said nitrogen-rich natural gas stream contains more than 2 mol percent of $C_5+$ hydrocarbons and is extracted in two stages with said physical solvent to remove $C_2+$ hydrocarbons and produce a residue natural gas stream primarily comprising nitrogen and methane for further extracting in said Step A of claim 1.

7. The process of claim 6, wherein:
   A. said nitrogen-rich natural gas stream contains said $C_2+$ hydrocarbons and acidic compounds which are extracted by said physical solvent and are present with said $C_2+$ hydrocarbons;
   B. said $C_2+$ hydrocarbons are compressed, cooled, condensed, and stripped to produce a sour natural gas liquid product containing said acidic compounds; and
   C. said sour natural gas liquid product is contacted with an aqueous amine solution to remove said acidic compounds and produce a sweet natural gas liquid product.

8. The process of claim 6, wherein said nitrogen-rich natural gas stream is extracted in the first stage of said two stages with a main solvent stream containing less than 15 mol % of $C_5+$ hydrocarbons to produce a partially stripped natural gas stream and a rich solvent stream containing said $C_2+$ hydrocarbons.

9. The process of claim 8, wherein said partially stripped natural gas stream is extracted in the second stage of said two stages with a lean-and-dry solvent stream, which is lean with respect to $C_1+$ hydrocarbons and dry with respect to water, to produce said residue natural gas stream, primarily comprising said nitrogen and said methane, and an enriched solvent stream.

10. The process of claim 9, wherein said enriched solvent stream is added to said main solvent stream in said first stage of said two stages for extracting said nitrogen-rich natural gas stream containing more than 2 mol percent of $C_5+$ hydrocarbons, whereby said rich solvent stream is produced.

11. The process of claim 1, wherein:
A. said nitrogen-rich natural gas stream contains acidic compounds which are extracted by said physical solvent and are present with said $C_1+$ hydrocarbons;
B. said $C_1+$ hydrocarbons are compressed and cooled to form a sour $C_1$-rich gas product comprising said acidic compounds; and
C. said sour $C_1$-rich gas product is contacted with an aqueous amine solution to remove said acidic compounds and produce a sweet $C_1$-rich gas product.

12. In a continuous process for producing a natural gas liquid hydrocarbon product having a selected composition, that is selectively adjustable to substantially any selected degree in accordance with market conditions, and a residue natural gas stream of pipeline quality, that selectively includes ethane ($C_2$), propane ($C_3$), and butane ($C_4$), by extraction of a natural gas stream, containing from 3 to 75 mol percent of nitrogen-rich, with a stream of a physical solvent to produce a rich solvent stream in addition to said residue natural gas stream, said rich solvent stream being flashed to at least atmospheric pressure to produce:
(a) a stream of $C_1$-rich flashed gases which are recycled for extraction with said physical solvent stream,
(b) a stream of $C_1$-lean flashed gases which are compressed, cooled, and condensed for demethanizing to produce a selected stream of $C_1$–$C_4$ rejected gases and said natural gas liquid product, and
(c) a recycle solvent stream that is split into a major solvent stream and a solvent slipstream which is regenerated to form a lean-and-dry solvent stream for recycling to said extraction,
wherein there exists a need for reducing the content of said nitrogen in said residue natural gas stream to less than 3 mol percent in order to obtain said pipeline quality,
an improvement which enables minor components of said nitrogen-rich natural gas stream to be removed in at least one extracting stage to produce a nitrogen-rich residue natural gas stream, consisting essentially of methane and said nitrogen, before isolating said nitrogen, said process comprising the following steps:
A. extracting said nitrogen natural gas stream with a stream of said physical solvent that selectively comprises said lean-and-dry solvent stream to produce said rich solvent stream and said residue natural gas stream;
B. extracting said residue natural gas stream with a sufficient quantity of said lean-and-dry solvent stream to extract said methane and to produce a $C_1$-rich solvent stream and a stream of said nitrogen; and C. flashing said $C_1$-rich solvent stream to produce a $C_1$-rich gas product and a dry stripped solvent stream.

13. The improved process of claim 9, wherein said lean-and-dry solvent stream contains less than 1 wgt. % of water and less than 1 volume % of $C_5+$ hydrocarbons.

14. The improved process of claim 13, wherein said nitrogen-rich natural gas stream contains water and more than 2 mol percent of $C_5+$ hydrocarbons and is extracted in two stages to remove said water and said $C_2+$ hydrocarbons, producing said residue natural gas stream.

15. The improved process of claim 14, wherein said nitrogen-rich natural gas stream is extracted with a main solvent stream containing less than 15 mol % of $C_5+$ hydrocarbons to produce a partially stripped natural gas stream and a rich solvent stream containing said water and said $C_2+$ hydrocarbons.

16. The improved process of claim 15, wherein said partially stripped natural gas stream is extracted with a lean-and-dry solvent stream, which is lean with respect to $C_1+$ hydrocarbons and dry with respect to water, to produce said residue natural gas stream and an enriched solvent stream.

17. The improved process of claim 16, wherein said enriched solvent stream is added to said main solvent stream for extracting said nitrogen-rich natural gas stream containing more than 2 mol percent of $C_5+$ hydrocarbons, whereby said rich solvent stream is produced.

18. The improved process of claim 17, wherein said rich solvent stream is flashed to produce said stream of $C_1$-rich flashed gases, said stream of $C_1$-lean flashed gases, and a wet stripped solvent stream.

19. The improved process of claim 16, wherein said enriched solvent stream is flashed to produce said stream of $C_1$-rich flashed gases, said stream of $C_1$-lean flashed gases, and a wet stripped solvent stream.

20. The improved process of claims 18 or 19, wherein said wet solvent stream is split to form said main solvent stream and said solvent slipstream which is regenerated to form said lean-and-dry solvent stream.

21. The process of claim 20, wherein said regenerating is done by distillation.

22. The improved process of claim 20, wherein said dry stripped solvent stream from said Step C contains less than 1 mol percent of $C_5+$ hydrocarbons and is split into a second solvent slipstream which is regenerated to form a part of said lean-and-dry solvent stream, the remaining portion of said stripped solvent stream being selectively combined with said lean-and-dry solvent stream from said regenerating.

23. The process of claim 1 or 12, wherein said inlet natural gas stream is selected from the group consisting of:
A. natural gas saturated with water;
B. natural gas at less than saturation with water;
C. sour natural gas;
D. sour natural gas which is pre-sweetened in gas phase with an aqueous amine solution;
E. sweet natural gas; and
F. dry natural gas.

24. The process of claim 23, wherein the volumes of said physical solvent streams for said extracting are determined by respective quantities of water, methane, nitrogen, $C_2$–$C_4$ hydrocarbons, and $C_5+$ hydrocarbons, loading capacities of said physical solvent for the hydrocarbons to be extracted, and relative solubilities in said physical solvent of the $C_1+$ hydrocarbons with respect to nitrogen.

25. The process of claim 23, wherein said physical solvent is selective toward ethane and heavier hydrocarbon components of said inlet natural gas stream over methane, such that the relative volatility of methane over ethane is at least 5.0 and the hydrocarbon loading capacity, defined as solubility of ethane in solvent, is at least 0.25 standard cubic feet of ethane per gallon of solvent.

26. The process of claim 25, wherein said physical solvent is selected from the group consisting of dialkyl ethers of polyalkylene glycol, N-methyl pyrrolidone, dimethyl formamide, propylene carbonate, sulfolane, and glycol triacetate.

27. The process of claim 26, wherein said solvent is selected from the group consisting of dimethyl ether of polyethylene glycol, dimethyl ether of polypropylene glycol, dimethyl ether of tetramethylene glycol, and mixture thereof.

28. The process of claim 27, wherein said solvent is dimethyl ether of polyethylene glycol containing 3–10 ethylene units and having a molecular weight of 146 to 476.

29. The process of claim 12, wherein said selected flashing pressures of said successive flashing stages vary between 1300 psia and 2 psia.

30. The process of claim 12, wherein said bottoms temperature of said demethanizing is varied between 0° F. and 300° F.

31. In a process for treating a nitrogen-rich hydrocarbon gas stream containing more than 3 mol % nitrogen, the improvement which comprises contacting said gas stream with a physical solvent, which is selective toward ethane and heavier hydrocarbon components of said hydrocarbon gas stream over methane, such that the relative volatility of methane over ethane is at least 5.0 and the hydrocarbon loading capacity of said solvent, defined as solubility of ethane in solvent, is at least 0.25 standard cubic feet of ethane per gallon of solvent, said contacting being at solvent flow rates selectively varying between 0.001 and 0.5 gallon/SCF of solvent of said hydrocarbon gas stream, to produce a hydrocarbon gas product meeting desired nitrogen specifications.

32. The improved process of claim 31, wherein said contacting comprises: (1) contacting said hydrocarbon gas stream with a first stream of said physical solvent to extract substantailly all $C_2+$ hydrocarbons in a rich solvent stream and to produce a methane-rich residue gas stream and (2) contacting said methane-rich gas stream with a second stream of said physical solvent to extract substantially all of said methane in a methane-rich solvent stream and to produce a nitrogen stream.

33. The improved process of claim 32, wherein said hydrocarbon gas stream is a wellhead natural gas stream and said improved process is operable at the wellhead, whereby said hydrocarbon gas product is suitable for pipeline shipment.

34. The process of claim 31, wherein said physical solvent is selected from the group consisting of dialkyl ethers of polyalkylene glycol, N-methyl pyrrolidone, dimethyl formamide, propylene carbonate, sulfolane, and glycol triacetate.

35. The process of claim 34, wherein said physical solvent is selected from the group consisting of dimethyl ether of polyethylene glycol, dimethyl ether of polypropylene glycol, dimethyl ether of tetramethylene glycol, and mixtures thereof.

36. The process of claim 35, wherein said physical solvent is dimethyl ether of polyethylene glycol containing 3–10 ethylene units and having a molecualr weight of 146 to 476.

* * * * *